(12) United States Patent
Hess et al.

(10) Patent No.: US 8,332,030 B2
(45) Date of Patent: Dec. 11, 2012

(54) DEVICE AND METHOD FOR PROVIDING ATRIAL-SYNCHRONIZED VENTRICULAR PACING WITH SELECTIVE ATRIAL TRACKING

(75) Inventors: Michael F. Hess, Minneapolis, MN (US); Eduardo N. Warman, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1962 days.

(21) Appl. No.: 11/115,597

(22) Filed: Apr. 27, 2005

(65) Prior Publication Data
US 2006/0247690 A1 Nov. 2, 2006

(51) Int. Cl.
*A61N 1/00* (2006.01)
(52) U.S. Cl. .................................. 607/9; 607/4; 607/11
(58) Field of Classification Search ................. 607/4, 9, 607/11
See application file for complete search history.

(56) References Cited

U.S. PATENT DOCUMENTS

| | | | |
|---|---|---|---|
| 4,624,260 A | 11/1986 | Baker et al. | |
| 4,951,667 A | 8/1990 | Markowitz et al. | |
| 5,144,949 A | 9/1992 | Olson | |
| 5,231,985 A | 8/1993 | Sutton et al. | |
| 5,480,413 A * | 1/1996 | Greenhut et al. | 607/14 |
| 5,540,725 A | 7/1996 | Bornzin et al. | |
| 5,601,613 A | 2/1997 | Florio et al. | |
| 5,893,882 A * | 4/1999 | Peterson et al. | 607/14 |
| 6,070,101 A * | 5/2000 | Struble et al. | 607/9 |
| 6,091,988 A * | 7/2000 | Warman et al. | 607/5 |
| 6,119,040 A | 9/2000 | Chirife | |
| 6,311,088 B1 * | 10/2001 | Betzold et al. | 607/14 |
| 6,411,848 B2 | 6/2002 | Kramer et al. | |
| 6,434,424 B1 | 8/2002 | Igel et al. | |
| 6,456,878 B1 * | 9/2002 | Yerich et al. | 607/9 |
| 6,609,028 B2 * | 8/2003 | Struble | 607/14 |
| 6,665,563 B2 * | 12/2003 | Stokes et al. | 607/3 |
| 6,876,881 B2 * | 4/2005 | Baumann et al. | 607/18 |
| 6,889,083 B2 * | 5/2005 | Kleckner et al. | 607/25 |
| 7,062,323 B2 | 6/2006 | Carlson et al. | |
| 2002/0082660 A1 | 6/2002 | Stahmann et al. | |
| 2004/0172076 A1 | 9/2004 | Stahmann et al. | |
| 2004/0193223 A1 * | 9/2004 | Kramer et al. | 607/9 |
| 2004/0210264 A1 * | 10/2004 | Kleckner et al. | 607/25 |
| 2004/0210266 A1 * | 10/2004 | Kramer | 607/25 |

FOREIGN PATENT DOCUMENTS
EP 0448139 A1 8/1991

* cited by examiner

*Primary Examiner* — Nicole F Lavert
(74) *Attorney, Agent, or Firm* — Reed A. Duthler; Stephen W. Bauer (57) ABSTRACT

A device for delivering pacing therapy includes an atrial and ventricular leads, sensing circuitry connected to the leads for detecting depolarizations, and pulse generation circuitry for delivering ventricular pacing pulses based on sensed atrial depolarizations. The device includes control circuitry for controlling the pulse generation circuitry in a first mode in which the pulse generation circuitry delivers atrial synchronized pulses to both the right and left ventricular leads in response to each atrial depolarization sensed. In response to a detected atrial arrhythmia, the control circuitry causes the pulse generation circuitry to deliver atrial synchronized ventricular pacing pulses in response only to selected atrial depolarizations.

4 Claims, 4 Drawing Sheets

DEVICE AND METHOD FOR PROVIDING ATRIAL-SYNCHRONIZED VENTRICULAR PACING WITH SELECTIVE ATRIAL TRACKING

BACKGROUND OF THE INVENTION

Bi-ventricular pacing, or cardiac resynchronization therapy (CRT), is a method of treating heart failure patients. CRT devices utilize electrical stimulation to resynchronize ventricular contractions with intrinsic or paced atrial contractions in individuals with electrical conduction disturbances.

Normally, electrical pulses originating in the atrium cause the contraction of both the right and left atrium. The contraction causes blood collected in the right and left atrium to be pumped into the right and left ventricles, respectively. The electrical signal continues to travel by way of conduction fibers to the right and left ventricles, causing them to contract. In order to maintain proper hemodynamic flow, it is important that the right and left ventricles contract after the right atrium and left atrium contract. The correct timing is normally maintained by the amount of time it takes electrical signals to conduct along high-speed fibers such as the Purkinje fibers. When damage to one of the high-speed fiber networks occurs, the ventricles may not contract at all or may contract at inappropriate times causing reduced hemodynamic flow.

CRT provides a solution to this problem by delivering atrial synchronized dual chamber bi-ventricular pacing. Typical CRT devices include an atrial sense amplifier to detect atrial depolarizations, a ventricular sense amplifier to detect ventricular depolarizations, and a ventricular pacing pulse generator. Upon sensing an atrial depolarization, a pulse is generated by the ventricular pacing pulse generator for delivery to the right and left ventricles. By maintaining proper Atrial-Ventricular (AV) delay, or AV synchrony, the CRT device ensures that both right and left ventricles contract at the appropriate time following an atrial contraction.

Problems arise, however, if intrinsic atrial depolarizations become too rapid, a condition known as an atrial arrhythmia. This results in rapid contractions of the ventricles prior to complete diastolic filling, resulting in diminished blood flow. In this scenario, current CRT devices respond by mode switching, which results in ventricular paces being delivered independent of intrinsic atrial depolarizations. This allows ventricular paces to be delivered at a rate that allows for complete diastolic filling, and improved blood flow. However, by disconnecting the timing between sensed atrial depolarizations and delivered ventricular pulses, the A-V timing discussed above is sacrificed.

BRIEF SUMMARY OF THE INVENTION

The present invention is a device and method that provides synchronous pacing between the atria and ventricles despite an atrial arrhythmia. Ventricular pacing pulses are generated at a rate less than the sensed atrial depolarizations during atrial arrhythmias, but maintain synchrony between atrial depolarizations and ventricular pulses.

DETAILED DESCRIPTION

Figure 1:
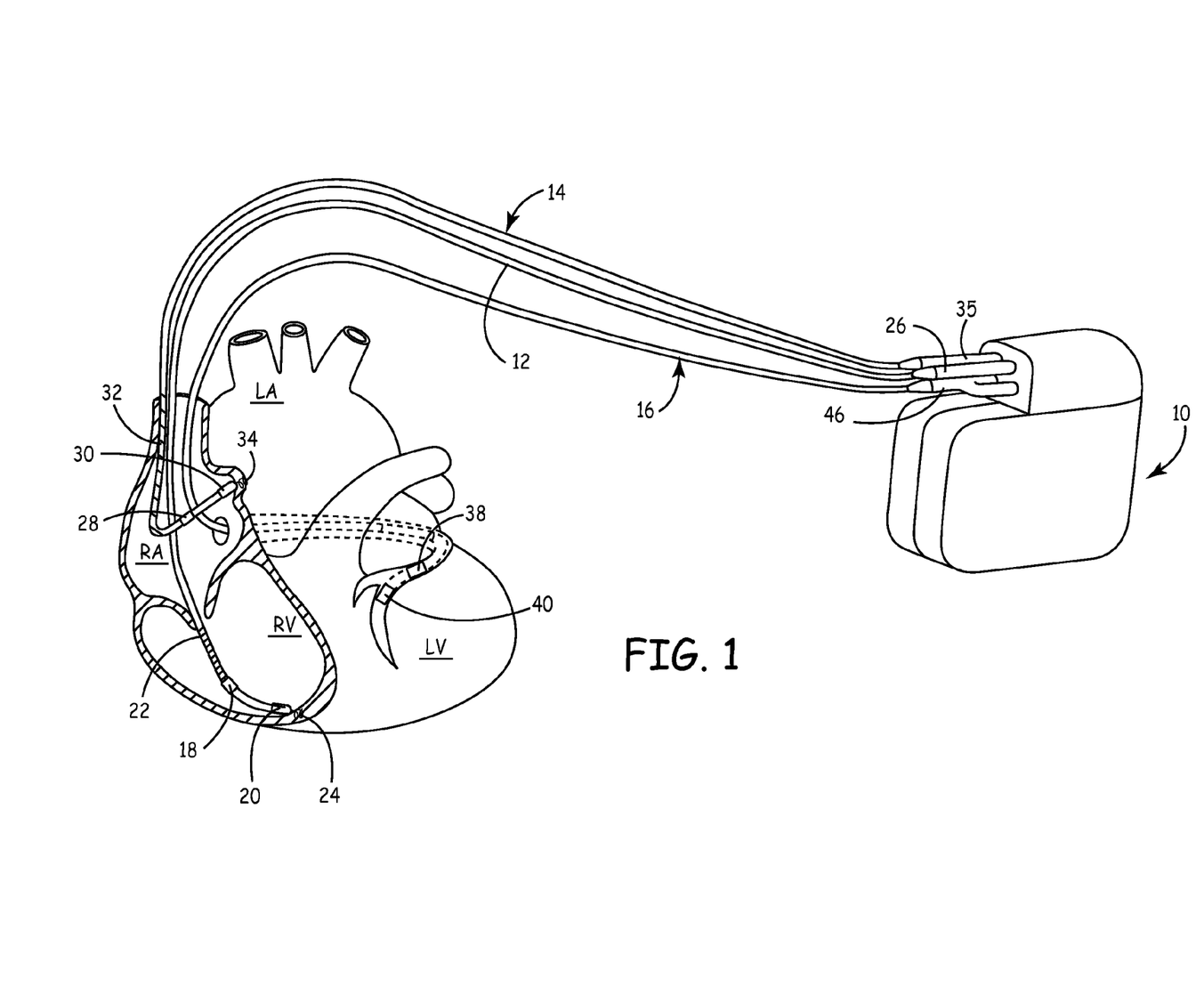
FIG. 1 shows a CRT device and lead set of a type in which the present invention may be practiced.

FIG. 1 shows implantable medical device (IMD) 10 including right ventricular lead 12, atrial/SVC lead 14, and left ventricular coronary sinus lead 16. IMD 10, in conjunction with leads 12, 14, and 16, is capable of providing cardiac resynchronization therapy (CRT). During normal operation IMD 10 provides bi-ventricular pacing in response to and synchronized with sensed atrial depolarizations. Synchronized bi-ventricular pacing means bi-ventricular paces follow atrial depolarizations (sensed or paced) by an appropriate Atrial-Ventricular (AV) interval. In response to a detected atrial arrhythmia, IMD 10 of the present invention switches from a one-to-one tracking algorithm in which each atrial sense results in synchronized bi-ventricular pacing, to a modified atrial tracking algorithm. With this modified tracking algorithm, IMD 10 still provides synchronized bi-ventricular pacing following an atrial sense; but rather than provide synchronized bi-ventricular pacing following each atrial sense, IMD 10 provides synchronized bi-ventricular pacing at a multiple of the one-to-one ratio. For instance, bi-ventricular paces may be provided in a 4:1 ratio in which a bi-ventricular pulse is provided synchronously following every fourth atrial depolarization sensed by IMD 10.

Right ventricular lead 12 is introduced through the superior vena cava (SVC) vein into the right atrium (RA), and then through the tricuspid valve into the right ventricle (RV). Located at the distal end of right ventricular lead 12 are ring electrode 18, tip electrode 20, elongated coil electrode 22, and distal attachment mechanism 24, which secures right ventricular lead 12 to the endocardial layer within the right ventricle. Located at the proximal end of right ventricular lead 12 is connector 26, which connects electrodes 18, 20 and 22 to circuitry within IMD 10. Electrodes 18 and 20 are used to deliver pacing pulses to the right ventricle as well as to sense electrical activity or R-wave depolarizations within the right ventricle. Elongated coil electrode 22 is used to provide cardioversion shocks if necessary.

Atrial/SVC lead 14 is threaded through the SVC vein into the right atrium. Located at the distal end of atrial/SVC lead 14 are ring electrode 28, tip electrode 30, and elongated coil electrode 32 and distal attachment mechanism 34 which secures atrial/SVC lead 14 to the endocardial layer within the right atrial wall. Located at the proximal end of atrial/SVC lead 14 is connector 35, which connects electrodes 28, 30 and 32 to circuitry within IMD 10. Electrodes 28 and 30 are used to deliver pacing pulses to the right atrium as well as to sense electrical activity or P-wave depolarizations within the right atrium.

Left ventricular coronary sinus lead 16 is introduced through the SVC vein into the right atrium, and then into the coronary sinus where it is placed inferiorly in the great vein such that ring electrode 38 and tip electrode 40 are located alongside the left ventricular chamber. Located at the proximal end of left ventricular coronary sinus lead 16 is connector 46, which connects electrodes 38 and 40 to circuitry within IMD 10. Electrodes 38 and 40 are used to deliver pacing pulses to the left ventricle as well as to sense electrical activity or R-wave depolarizations within the left ventricle (LV).

Figure 2:
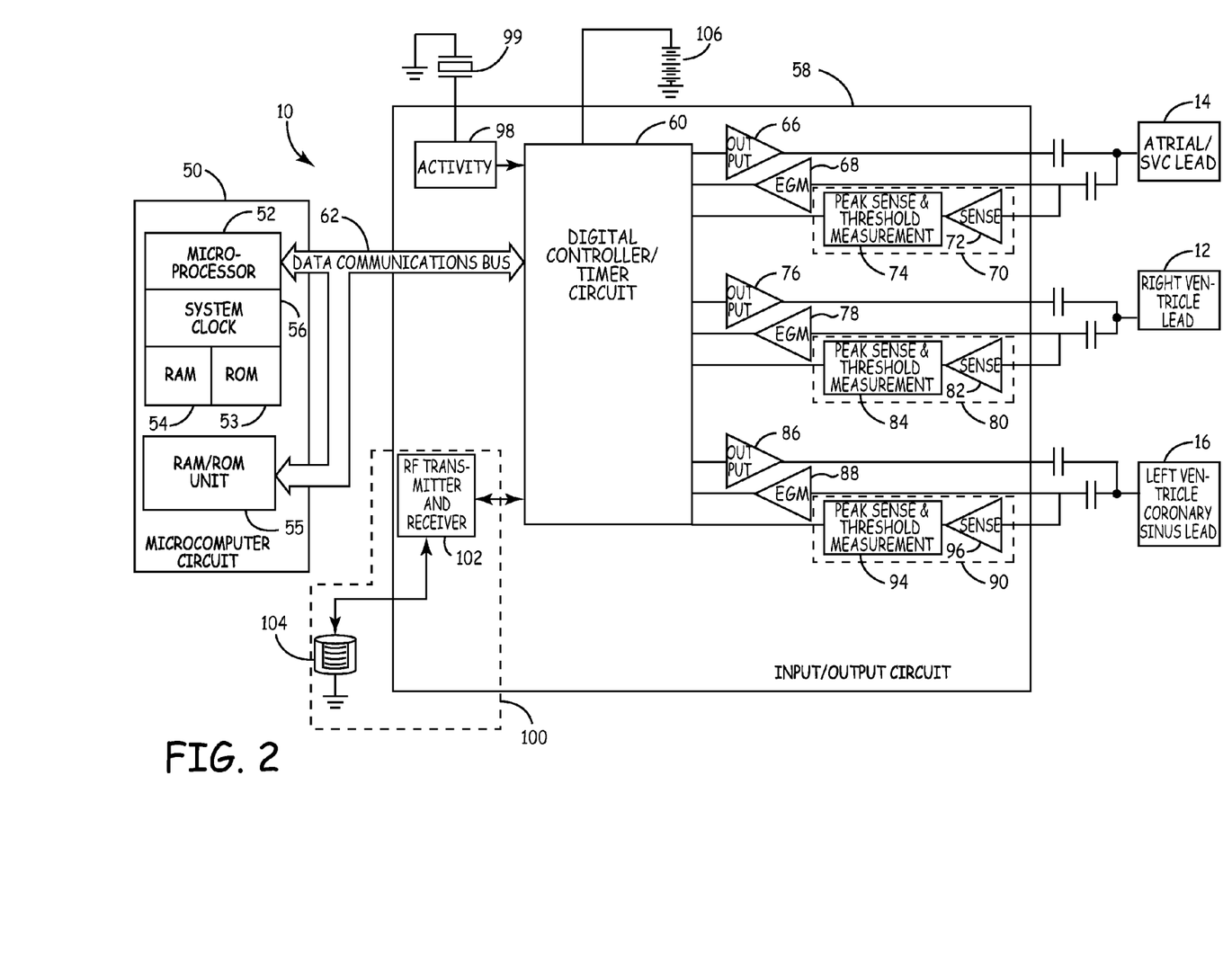
FIG. 2 is a functional block diagram of circuitry located within the CRT device.

FIG. 2 is a functional block diagram of circuitry located within IMD 10. The circuitry of IMD 10 is a microprocessor based system, with microcomputer circuit 50 including microprocessor 52, on-board memory including ROM memory 53 and RAM memory 54, off-board RAM/ROM memory 55 and system clock 56. IMD 10 also includes input/output circuit 58, having digital controller/timer circuit 60 connected to microcomputer circuit 50 via data communications bus 62. Microcomputer circuit 50, specifically processor 52, communicates with input/output circuit 58 to monitor electrical activity in the heart as well as to deliver appropriately timed pulses from IMD 10 to the various electrodes. Digital controller/timer circuit 60 includes digital timers and counters used to determine time between successive depolarizations in the atria and ventricles as well as to provide various refractory, blanking and other timing windows used to determine delivery of paced pulses to the atria and ventricles. Digital controller/timer circuit 60 receives sensed activity signals and causes pacing pulses to be delivered via connections to leads 12, 14, and 16.

Atrial/SVC lead 14 is connected to digital controller/timer circuit 60 via pace output generator 66, EGM amplifier 68, and sensing circuitry 70, including sense amplifier 72 and peak sense and threshold measurement unit 74. Sense amplifier 70 amplifies sensed electrical cardiac signals from atrial/SVC lead 14 and provides an amplified signal to peak sense and threshold measurement circuitry 74, which in turn provides an indication of peak sense voltages and measured sense amplifier threshold voltages to digital controller/timer 60. Electrical signals sensed from atrial/SVC lead 14 provide IMD 10 with information regarding depolarizations in the atrium. Sensed signals from atrial/SVC lead 14 are also provided to EGM amplifier 68, which provides an electrogram signal when IMD 10 is being interrogated by an external programmer to transmit a representation of a cardiac analog electrogram. Under the control of digital controller/timer circuit 60, output pulse generator 66 provides pacing pulses to atrial/SVC lead 14.

Right ventricular lead 12 is connected to digital controller/timer circuit 60 via pace output generator 76, EGM amplifier 78, and sensing circuitry 80, including sense amplifier 82 and peak sense and threshold measurement unit 84. Sense amplifier 82 amplifies sensed electrical cardiac signals from right ventricular lead 12 and provides an amplified signal to peak sense and threshold measurement circuitry 84, which in turn provides an indication of peak sense voltages and measured sense amplifier threshold voltages to digital controller/timer 60. Electrical signals sensed from right ventricular lead 12 provide IMD 10 with information regarding depolarizations in the right ventricle. Sensed signals from right ventricular lead 12 are also provided to EGM amplifier 78, which provides an electrogram signal when IMD 10 is being interrogated by an external programmer to transmit a representation of a cardiac analog electrogram. Under the control of digital controller/timer circuit 60, output pulse generator 76 provides pacing pulses to right ventricular lead 12.

Coronary sinus lead 16 is also connected to an output pulse generator 88, EGM amplifier 90, and sensing circuitry 90, including sense amplifier 92, and peak sense and threshold measurement unit 94. Sense amplifier 96 amplifies sensed electrical cardiac signals and provides an amplified signal to peak sense and threshold measurement circuitry 94, which in turn provides an indication of peak sense voltages and measured sense amplifier threshold voltages to digital controller/timer 60. Sensed signals from coronary sinus lead 16 are also provided to EGM amplifier 88, which provides an electrogram signal when IMD 10 is being interrogated by an external programmer to transmit a representation of a cardiac analog electrogram. Output pulse generator 88 provides pacing pulses to coronary sinus lead 16 under the control of digital controller/timer circuit 60. For instance, digital controller/timer circuit 60 may cause output pulse generator 86 to provide a pulse to coronary sinus lead 16 in response to a pacing trigger signal provided each time the escape interval times out, in response to an externally transmitted pacing command, or in response to other stored commands as is well known in the pacing art.

In the embodiment shown in FIG. 2, IMD 10 also includes activity sensor 98 and accelerometer 99 which provide input to digital controller/timer circuit 60 regarding a patient's metabolic requirements. Digital controller/timer circuit 60 takes into account input from activity sensor 98 and accelerometer 99 in deciding the appropriate rate at which to provide pulses to atrial/SVC lead 14, right ventricular lead 12 and left ventricular coronary sinus lead 16.

IMD 10 also includes telemetry circuitry 100, RF transmitter and receiver 102, and antenna 104, which allows IMD 10 to be programmed by means of an external programming unit (not shown). Power is supplied to all systems of IMD 10 by power supply 106.

Bi-ventricular pacing therapy provided by IMD 10 requires constant pacing of both the right and left ventricles in order to maintain proper hemodynamic flow. A number of different pacing modes exist depending on the situation. Digital controller/timer circuit 60 of FIG. 2 includes programmable digital counters which control the basic timing intervals associated with each of the various modes of bi-ventricular pacing. Each mode can be described by a three (sometimes four) letter code as described in table 1 below.

TABLE 1

| | Mode Code | | |
|---|---|---|---|
| | 1 | 2 | 3 |
| Function | Chamber Paced | Chamber Sensed | Response to Sensing |
| Options | A - Atrium | A - Atrium | T - Triggered |
| | V - Ventricular | V - Ventricular | I - Inhibited |
| | D - Both | D - Both | D - Both |

For example, when in DDD mode, IMD 10 paces either chamber (atrium or ventricle) and senses in either chamber (atrium or ventricle). In response to sensed depolarizations, pulses may be triggered or inhibited. Thus, IMD 10 in DDD mode may deliver pacing pulses to ventricular leads 12 and 16 in response to electrical activity sensed in the atrium. This is a common scenario during normal operation, and DDD mode is often used to maintain proper coordination between atrial contractions and ventricular contractions. Monitoring of atrial depolarizations is provided by sense circuitry 70 which receives signals from atrial/SVC lead 14 and communicates the sensed signal to digital controller/timer circuit 60. In response to a sensed atrial depolarization, digital controller/timer circuit 60 causes pace output generators 76 and 86 to provide a pulse to right ventricular lead 12 and coronary sinus lead 16, resulting in contraction of both ventricles. Thus, in DDD mode, paced ventricular contractions are coordinated and provided synchronously with each sensed atrial contraction.

During atrial arrhythmias such as supraventricular tachycardia (SVT), atrial fibrillation (AF) and atrial flutter, atrial depolarizations come more rapidly. If IMD 10 is allowed to remain in DDD mode, rapid atrial depolarizations result in IMD 10 providing paced pulses to ventricular leads 12 and 16 at a rate corresponding to an Upper Tracking Rate (UTR). The upper tracking rate essentially dictates a minimum amount of time that must pass between successive ventricular pulses provided by IMD 10. The upper tracking interval therefore prevents ventricular pacing pulses from being provided in rapid succession based on sensed atrial depolarizations. If an atrial depolarization is sensed by IMD 10 before the upper tracking interval has expired from the last ventricular pacing pulse provided, the subsequent ventricular pacing pulse is delayed until the end of the upper tracking rate. The delay until the upper tracking interval expires results in asynchrony between the sensed atrial depolarization and the ventricular pacing pulse. Asynchronous pacing of the right and left ventricles disrupts the timing of the heart and decreases overall hemodynamic flow. If the arrhythmia persists, ventricular pacing pulses will be provided asynchronously at a rate defined by the upper tracking interval, generally much faster than desired.

Typical responses to atrial arrhythmias in the prior art involve mode switching, generally defined as switching from a first pacing mode (such as DDD or VDD) that paces at least one ventricle based on sensed atrial activity, to a second pacing mode (such as DDI or VVI) that paces at least one ventricle at a predetermined lower rate with such pacing inhibited based on intrinsic ventricular activity. Inhibited means that a ventricular pace is provided by IMD 10 only if no intrinsic ventricular depolarization is sensed by IMD 10. After a mode switch, ventricular pacing transitions slowly and smoothly to a rate lower than the upper tracking rate, although ventricular paces no longer track atrial depolarizations. While mode switching allows for more complete diastolic filling than would be possible without a mode switch, the downside is ventricular contractions are no longer synchronized to follow atrial contractions.

The present invention provides an alternative to traditional mode switching after detection of an arrhythmia. In one embodiment, IMD 10 provides traditional mode switching if the arrhythmia is classified as irregular, and provides a modified atrial tracking therapy of the present invention if classified as regular. Mode switching may be more beneficial to a patient with a highly irregular arrhythmia, while the modified tracking therapy of the present invention will be more beneficial the more regular the arrhythmia. However, this does not mean that irregularity precludes the use of the modified tracking therapy of the present invention, although it may be more beneficial for more regular arrhythmias. In one embodiment, regularity is determined by measuring time intervals between a number of recent atrial depolarizations and comparing the difference between the largest time interval between successive atrial depolarizations and the smallest time interval between successive atrial depolarizations. If the difference between the two is greater than a predetermined reference value, then IMD 10 determines the arrhythmia is irregular and provides a mode switch. Likewise, if the difference between the two is less than the predetermined reference value, then IMD 10 determines the arrhythmia is regular and provides for modified atrial tracking of the present invention. Regularity may be determined in a number of ways, for example the following equation provides another measure of the regularity of an arrhythmia.

EQ 1:
$$\frac{\text{(Second Largest Interval} - \text{Second Smallest Interval)}}{\text{Median Interval}} < 25\%$$

Equation 1 divides the difference between the second largest interval and the second smallest interval (excluding the extreme largest interval and extreme smallest interval) by the median interval. If the result is less than 25% the arrhythmia is classified as regular, and if it is more than 25% it is classified as irregular. The 25% used in this embodiment is an example of how the determination of regularity works, that value can be different depending on the application. If an arrhythmia is regular, then IMD 10 maintains A-V synchrony by providing a modified tracking therapy of the present invention. In other embodiments, IMD 10 may provide ventricular rate regularization therapy (VRR) in place of the mode switching discussed above.

If IMD 10 senses an atrial arrhythmia that it classifies as regular, rather than provide mode switching as discussed above, IMD 10 provides a modified tracking therapy in which synchronous bi-ventricular paces are provided in response to atrial depolarizations, but not in the one-to-one ratio provided during normal operation. Thus, IMD 10 of the present invention provides an alternative to mode switching.

Figure 3:
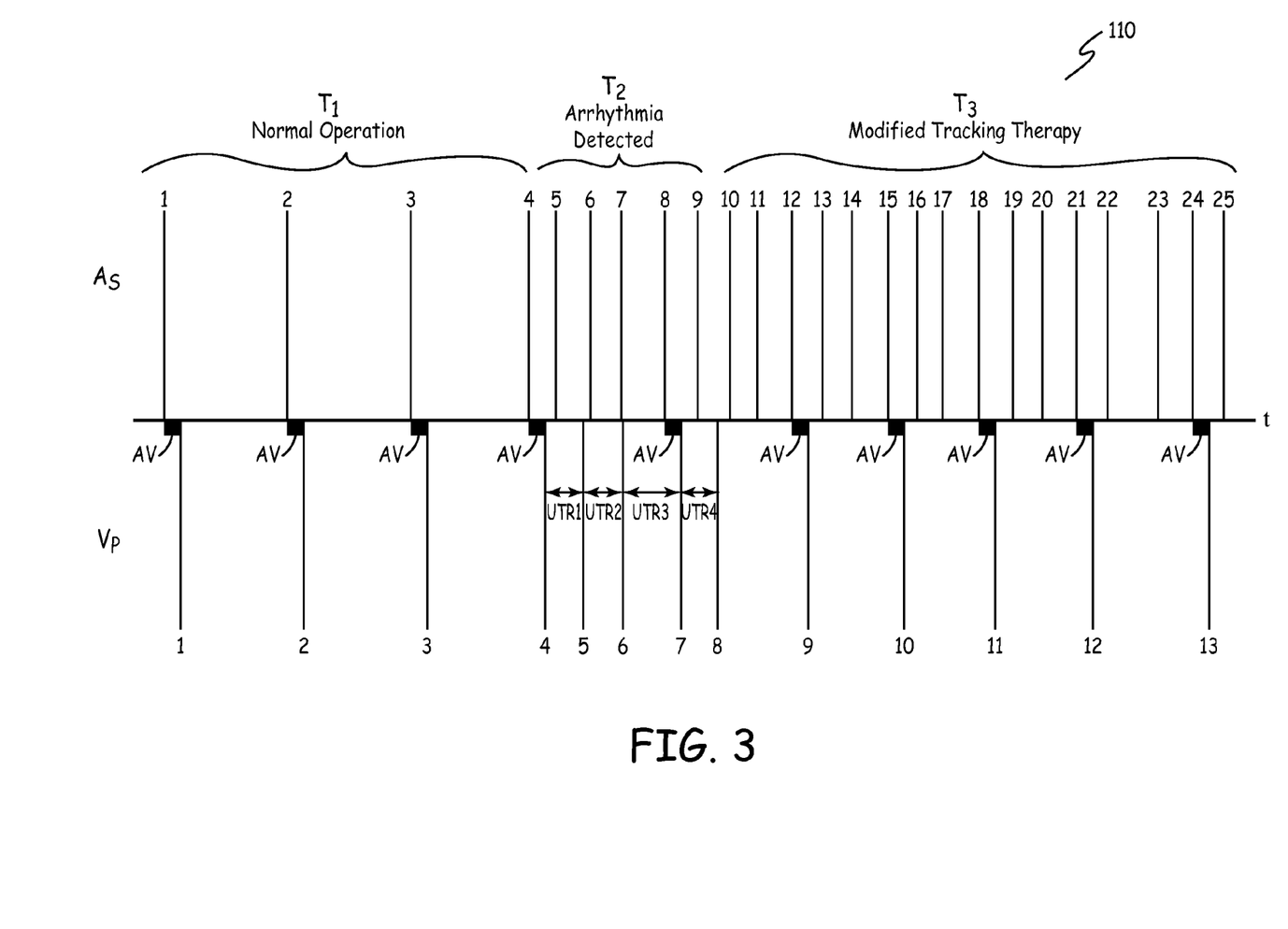
FIG. 3 is a chart illustrating the timing between sensed atrial events and paced ventricular events according to the present invention.

FIG. 3 shows an A-V waveform illustrating an embodiment of the present invention. Waveform 110 shows both atrial depolarizations As (top bars) and bi-ventricular paces Vp (bottom bars) along timeline t. Bi-ventricular paces Vp correspond to paces generated and delivered by IMD 10 to right ventricular lead 12 and coronary sinus lead 16. Although shown as being delivered simultaneously, in one embodiment there is a timed delay between the pulse delivered to right ventricular lead 12 and the pulse delivered to coronary sinus lead 16. During time period T1, IMD 10 is operating under non-arrhythmia circumstances, in which each intrinsic atrial depolarization $As_1$, $As_2$, $As_3$ and $As_4$ is followed by a respective bi-ventricular paces $Vp_1$, $Vp_2$, $Vp_3$ and $Vp_4$ from IMD 10, assuming no intrinsic ventricular depolarization is sensed by IMD 10. During this time, bi-ventricular paces Vp are delivered by IMD 10 synchronously with atrial depolarizations As sensed by IMD 10, and each bi-ventricular pace Vp is provided a set amount of time, known as atrioventricular delay (labeled AV in FIGS. 3 and 4), following each atrial depolarization.

During time period T2, IMD 10 senses an atrial arrhythmia, characterized by a decrease in time between atrial depolarizations $As_4$, $As_5$, $As_6$, $As_7$, $As_8$, $As_9$. IMD 10 monitors the rate of atrial depolarizations to determine whether the arrhythmia is regular or irregular. During the arrhythmia, but before IMD 10 has decided the proper course of action, bi-ventricular paces provided by IMD 10 are constrained by the Upper Tracking Rate (UTR). The UTR prevents bi-ventricular paces Vp from being provided at a rate equal to the rate of the arrhythmia. The UTR is provided following every bi-ventricular pulse, although during time T1 the UTR following each bi-ventricular pace had timed out before the next atrial depolarization was sensed. Atrial depolarization $As_5$ is sensed by IMD 10 before UTR1 has timed out, causing IMD 10 to delay delivery of bi-ventricular pace $Vp_5$. Atrial depolarization $As_6$ is also sensed by IMD 10 before UTR2 has timed out, causing IMD 10 to delay delivery of bi-ventricular pace $Vp_6$. Before UTR2 has timed out IMD 10 also senses $As_7$, which does not invoke any response by IMD 10. Atrial depolarization $As_8$ is sensed by IMD 10 after UTR3 has timed out, resulting in delivery of bi-ventricular pace $Vp_7$ at the appropriate AV delay following $As_8$. Atrial depolarization $As_9$ is sensed by IMD 10 before UTR4 has timed out, causing IMD 10 to delay delivery of bi-ventricular pace $Vp_8$ until UTR4 terminates. As shown during time T2 in FIG. 3, during an atrial arrhythmia bi-ventricular pulses Vp are generally provided at a rate equal to the upper tracking rate, generally faster than desired by IMD 10. Furthermore, during an atrial arrhythmia bi-ventricular pulses Vp are provided asynchronously with atrial depolarizations As. That is, bi-ventricular pulses Vp do not follow atrial depolarizations As at the appropriate AV delay time. If classified as irregular, IMD 10 proceeds to mode switch and may begin VRR therapy as known in the prior art. If classified as regular, IMD 10 begins a modified atrial tracking as shown in FIG. 3.

In one embodiment shown in FIG. 3, IMD 10 provides bi-ventricular paces at a defined ratio with respect to atrial depolarizations. For example, if IMD 10 determines the rate of the atrial arrhythmia to be 210 bpm, and IMD 10 determines based on input from activity sensor 98 that the appropriate number of beats per minute should be around 60 beats a minute, IMD will provide bi-ventricular paces at a ratio of 3:1. If bi-ventricular pulses are provided at a ratio of 3:1, then after every third atrial depolarization sensed, IMD 10 will provide a corresponding ventricular pulse to both the right and left ventricle, at the appropriate AV delay interval. At 3:1, bi-ventricular pulses will be provided at a rate of approximately 70 beats per minute. For example, following the sense of atrial depolarizations $As_{10}$, $As_{11}$ and $As_{12}$ IMD 10 provides bi-ventricular pulse $Vp_9$ synchronized with atrial depolarization $As_{12}$. The pulse is synchronized because $Vp_9$ is delivered at the proper AV interval following $As_{12}$. After sensing atrial depolarizations $As_{13}$, $As_{14}$, and $As_{15}$ (three atrial depolarizations), IMD 10 delivers another bi-ventricular pulse $Vp_{10}$ synchronized with atrial depolarization $As_{15}$. After sensing atrial depolarizations $As_{16}$, $As_{17}$, and $As_{18}$ (three atrial depolarizations), IMD 10 delivers another bi-ventricular pulse $Vp_{11}$ synchronized with atrial depolarization $As_{18}$. After sensing atrial depolarizations $As_{19}$, $As_{20}$, and $As_{21}$ (three atrial depolarizations), IMD 10 delivers another bi-ventricular pulse $Vp_{12}$ synchronized with atrial depolarization $As_{21}$. After sensing atrial depolarizations $As_{22}$, $As_{23}$, and $As_{24}$ (three atrial depolarizations), IMD 10 delivers another bi-ventricular pulse $Vp_{13}$ synchronized with atrial depolarization $As_{24}$.

In the embodiment shown in FIG. 3, the AV delay during modified atrial tracking (at time T3) is the same AV delay used during normal operations (at time T1). In other embodiments, the AV delay employed during modified atrial tracking is different, either longer or shorter, than the AV delay used during normal operations. In one embodiment, the AV delay during modified atrial tracking would be zero, meaning bi-ventricular pulses would be provided simultaneously with atrial depolarizations. In other embodiments synchronous bi-ventricular pulses may be provided at an AV delay or interval that is different than the AV delay or interval used during normal operations.

The modified tracking therapy employed by IMD 10 provides bi-ventricular pacing at a rate that is closer to the desired ventricular pacing rate as well as synchronized with sensed atrial depolarizations. There are a number of ways to decide what is closest to the desired ventricular pacing rate, one such method is shown in Equation 2 below.

EQ. 2:
$$N < \frac{\text{Arrhythmia Rate (bpm)}}{\text{Sensor Rate (bpm)}}$$

Solving equation 2 for the largest N (whole number) that still satisfies the equation provides for bi-ventricular pacing as close as possible to the desired bi-ventricular pacing rate without going below the desired bi-ventricular pacing rate. N is the selected ratio (N:1) of number of atrial pulses sensed for every one bi-ventricular pulse delivered. Arrhythmia Rate is the calculated rate of atrial depolarizations per minute during the arrhythmia, and sensor rate is the optimal ventricular pacing rate as dictated by activity sensor 98 within IMD 10. N is selected to be as large as possible such that the equation is still satisfied. For example, if IMD 10 selects 60 bpm as the sensor rate (optimal ventricular pacing rate) and IMD 10 determines the rate of the arrhythmia is 250 bpm, then N must be less than 4.166, resulting in a 4:1 ratio being selected. In this way, IMD 10 provides a relatively constant ventricular pacing at an appropriate pace (as dictated by EQ. 2), while maintaining coordination (synchronization) between atrial depolarizations (and thus contractions) and ventricular depolarizations (and thus contractions). In another embodiment, equation 2 is modified such that N must be greater than the arrhythmia rate divided by the sensor rate. In this case, the smallest N that satisfies the relationship is selected and bi-ventricular paces will be provided closest to the desired ventricular pacing rate without exceeding the desired ventricular pacing rate.

In this embodiment, IMD 10 also monitors the rate of the arrhythmia by continuing to measure the time between successive atrial depolarizations. If IMD 10 detects a change in atrial rate, then IMD 10 may modify the ratio between atrial depolarizations and bi-ventricular pacing pulses. For instance, if the atrial arrhythmia decreases from 210 beats a minute to 150 beats a minute, then IMD 10 will modify the ratio from 3:1 to 2:1, meaning bi-ventricular pacing will be provided for every other sensed atrial depolarization, resulting in bi-ventricular pacing rate of 75 beats a minute. Likewise, if IMD 10 detects the arrhythmia has ended, then IMD 10 will return to providing a bi-ventricular pulse following each sensed atrial depolarization as shown at time T1 in FIG. 3.

Figure 4:
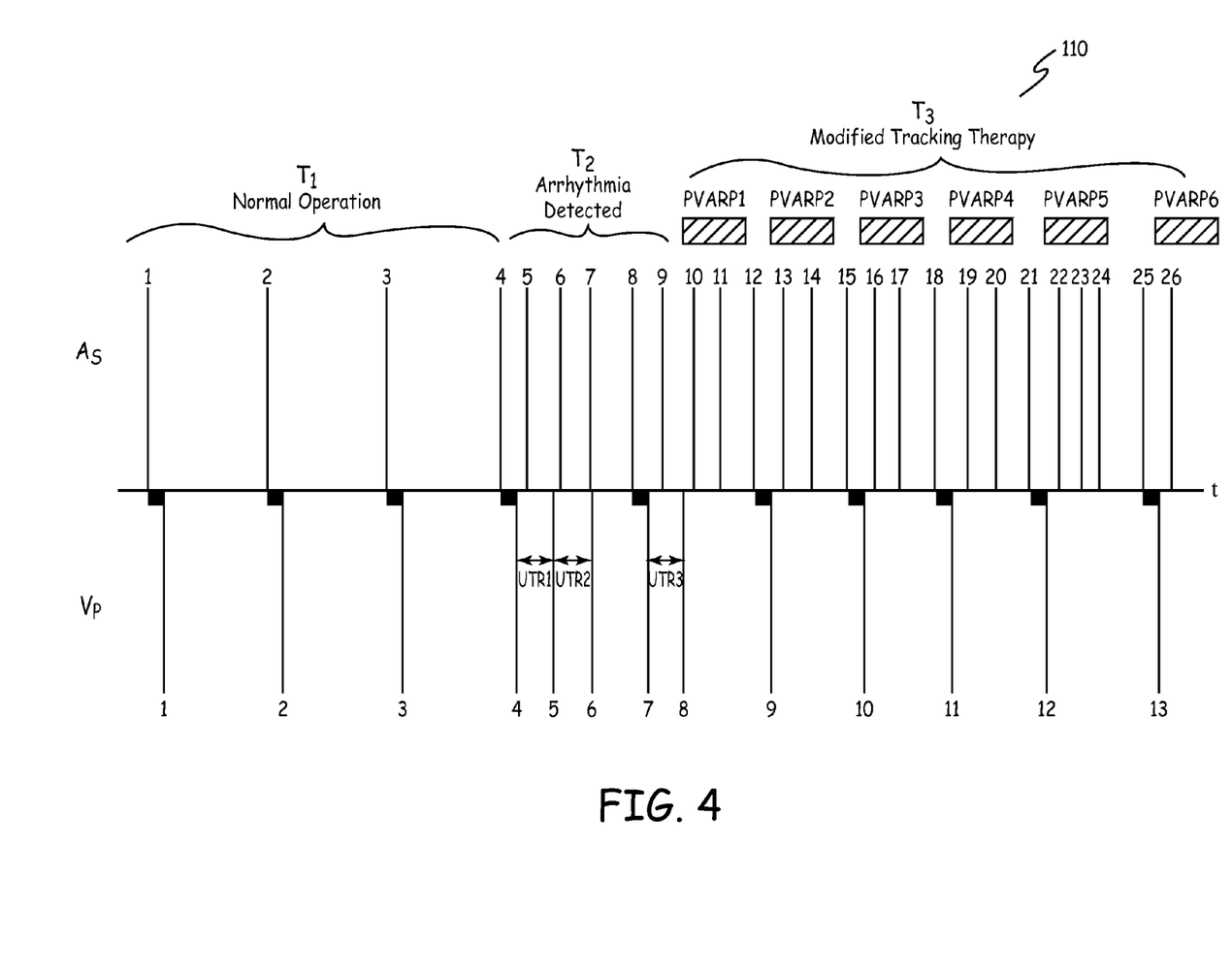
FIG. 4 is a chart illustrating the timing between sensed atrial events and paced ventricular events according to the present invention.

FIG. 4 illustrates another embodiment, in which IMD 10 accomplishes the same result in a slightly different manner. FIG. 4 implements the modified tracking therapy by extending the post ventricular atrial refractory period (PVARP). PVARP is a programmable interval following a ventricular event when the atrial channel is refractory to sensed events, meaning that sensed atrial depolarizations do not result in ventricular pacing pulses. During typical operation during time T1, PVARP is very short and prevents atrial sensing of far-field signals and retrograde P-waves that may be mistaken for atrial depolarizations resulting in closely coupled ventricular pulses. By extending the PVARP interval during modified tracking therapy, PVARP is used to prevent ventricular pacing in response to each atrial depolarization sensed during an arrhythmia. Waveform 112 shows both atrial depolarization As (top bars) and bi-ventricular paces Vp (bottom bars) along timeline t. Bi-ventricular paces Vp correspond to paces generated and delivered by IMD 10. During time period T1, IMD 10 is operating under non-arrhythmia circumstances, in which each intrinsic atrial depolarization $As_1$, $As_2$, $As_3$ and $As_4$ is followed by a respective bi-ventricular pace $Vp_1$, $Vp_2$, $Vp_3$ and $Vp_4$ from IMD 10. Bi-ventricular paces $Vp_1$, $Vp_2$, $Vp_3$, and $Vp_4$ are provided by IMD 10 at a set interval (AV) following each atrial depolarization, resulting in synchronous delivery of bi-ventricular pacing pulses. During this time, PVARP is very short and is used in the typical fashion to prevent atrial sensing of far-field signals and retrograde P-waves.

During time period T2, IMD 10 senses an atrial arrhythmia, characterized by a decrease in time between atrial depolarizations $As_4$, $As_5$, $As_6$, $As_7$, $As_8$, $As_9$. As described above with respect to FIG. 3, during an arrhythmia but before IMD 10 has provided a mode switch or modified tracking therapy, bi-ventricular paces will be provided at a rate roughly equal to the Upper Tracking Limit (UTR). This rate is typically much faster than desired by IMD 10, and does not provide for synchronous delivery of bi-ventricular paces with respect to sensed atrial depolarizations. IMD 10 monitors the pace of atrial depolarizations during time period T2 to determine whether the arrhythmia is regular or irregular. If classified as irregular, IMD 10 proceeds to mode switch and may begin VRR therapy.

If the atrial activity is classified as regular, IMD 10 begins a modified atrial tracking. If IMD 10 determines based on input from activity sensor 98 that the appropriate number of beats per minute should be around 60 beats a minute, IMD 10 will extend PVARP following each bi-ventricular pulse to an interval that prevents IMD 10 from providing ventricular paces in response to sensed atrial events at a pace much greater than 60 beats a minute. As stated above, during PVARP, bi-ventricular pulses are not delivered in response to sensed atrial depolarizations. For example, after switching to the modified atrial tracking mode, IMD 10 delivers ventricular pulse $Vp_8$ to right and left ventricular leads 12 and 16 respectively following sensed atrial depolarization $As_9$, followed by PVARP1 in which sensed atrial depolarizations $As_{10}$ and $As_{11}$ do not result in bi-ventricular pacing pulses being delivered. After PVARP1 ends, the next atrial depolarization $As_{12}$ is followed by bi-ventricular pacing pulse $Vp_7$ at the appropriate AV interval (providing AV synchrony) and PVARP2. During PVARP2, atrial depolarizations $As_{13}$ and $As_{14}$ sensed by IMD 10 do not result in delivery of bi-ventricular pulses. After PVARP2 ends, the next atrial depolarization $As_{15}$ sensed by IMD 10 results in delivery of bi-ventricular pacing pulse $Vp_{10}$ followed by PVARP3. During PVARP3, atrial depolarizations $As_{16}$ and $As_{17}$ sensed by IMD 10 do not result in delivery of bi-ventricular pulses. After PVARP3 ends, the next atrial depolarization $As_{18}$ sensed by IMD 10 results in delivery of bi-ventricular pacing pulse $Vp_{11}$ followed by PVARP4. Notice during PVARP5, three atrial depolarizations $As_{22}$, $As_{23}$, and $As_{24}$ are sensed by IMD 10, rather than two as in the previous PVARP intervals shown in FIG. 4. Bi-ventricular pacing pulse $Vp_{13}$ is not provided until PVARP5 ends and IMD 10 senses atrial depolarization $As_{25}$. This is slightly different that the embodiment shown in FIG. 3 which provides bi-ventricular paces following a certain number of sensed atrial depolarizations. This embodiment creates an interval during which sensed atrial depolarizations do not result in bi-ventricular pacing pulses being delivered. In this way, each ventricular pace is synchronized with atrial depolarizations at the appropriate AV delay interval, but the PVARP prevents bi-ventricular paces from being delivered after every sensed atrial depolarization during an atrial arrhythmia.

The present invention therefore provides an alternative to mode switching when IMD 10 detects an atrial arrhythmia characterized by a regular rhythm. When a regular atrial arrhythmia is detected, IMD 10 switches from a mode in which each atrial depolarization sensed results in delivery of a synchronized bi-ventricular pulse to a modified tracking mode in which delivery of bi-ventricular pulses are synchronized with selected atrial pulses. In this way, the present invention provides AV synchrony between selected atrial depolarizations and ventricular pacing pulses during atrial arrhythmia.

Although the present invention has been described with reference to preferred embodiments, workers skilled in the art will recognize that changes may be made in form and detail without departing from the spirit and scope of the invention. For example, although IMD 10 has been described as providing bi-ventricular pacing, the present invention is also applicable to devices that provide pacing pulses to one ventricle.

The invention claimed is:

1. A device for providing pacing therapy, the device comprising:
    an atrial lead for sensing electrical activity in an atrium;
    a ventricular lead for sensing electrical activity in a ventricle and for delivering electrical pulses to the ventricle;
    sensing circuitry connected to the atrial and ventricular leads for sensing depolarizations in the atrium and ventricle, respectively;
    pulse generation circuitry connected to the ventricular lead for delivering pacing pulses to the ventricle, respectively; and
    control circuitry responsive to sensed atrial depolarizations, for detecting atrial arrhythmias and for controlling the pulse generation circuitry in a mode in which the pulse generation circuitry delivers an atrial synchronized pulse to the ventricular lead in response to each atrial depolarization and causing the pulse generation circuitry, in response to a detected atrial arrhythmia, to deliver atrial synchronized pacing pulses to the ventricular lead in response only to selected atrial depolarizations, wherein the control circuitry determines a desired ratio of atrial depolarizations to ventricular paced pulses based on a beat rate of the atrial arrhythmia and a preferred ventricular beat rate and causes the pulse generation circuitry to deliver atrial synchronized pulses to the ventricular lead in response to detection of a number of atrial depolarizations corresponding to the desired ratio.

2. The device of claim 1, wherein if the desired ratio of atrial depolarizations to ventricular paced pulses is determined to be N-to-one, where N is an integer, then the control circuitry causes the pulse generation circuitry to deliver the atrial synchronized pulse to the ventricular lead in response to each Nth atrial depolarization detected.

3. A device for providing pacing therapy, the device comprising:
    an atrial lead for sensing electrical activity in an atrium;
    a right ventricular lead for sensing electrical activity in a right ventricle and for delivering electrical pulses to the right ventricle;
    a left ventricular lead for sensing electrical activity in a left ventricle and for delivering electrical pulses to the left ventricle;
    sensing circuitry connected to the atrial, right ventricular and left ventricular leads for sensing atrial and ventricular depolarizations;
    pulse generation circuitry connected to the right ventricular and left ventricular leads for delivering pacing pulses to the right ventricle and left ventricle, respectively; and
    control circuitry responsive to sensed atrial depolarizations, for detecting atrial arrhythmias and for controlling the pulse generation circuitry in a mode in which the pulse generation circuitry delivers atrial synchronized pulses to both the right and left ventricular leads in response to each atrial depolarization and causing the pulse generation circuitry, in response to a detected atrial arrhythmia, to deliver atrial synchronized pacing pulses to both the right and left ventricular leads in response only to selected atrial depolarizations, wherein the control circuitry determines a desired ratio of atrial depolarizations to ventricular paced pulses based on a beat rate of the atrial arrhythmia and a preferred ventricular beat rate and causes the pulse generation circuitry to deliver atrial synchronized pulses to the right and left ventricular leads in response to detection of a number of atrial depolarizations corresponding to the desired ratio.

4. The device of claim 3, wherein if the desired ratio of atrial depolarizations to ventricular paced pulses is determined to be N-to-one, where N is an integer, then the control circuitry causes the pulse generation circuitry to deliver the atrial synchronized pulse to the right and left ventricular leads in response to each Nth atrial depolarization sensed.

* * * * *